United States Patent
Shin et al.

(10) Patent No.: US 7,348,475 B2
(45) Date of Patent: Mar. 25, 2008

(54) TRANSGENIC RICE LINE PRODUCING HIGH LEVEL OF FLAVONOIDS IN THE ENDOSPERM

(75) Inventors: Young-Mi Shin, Kwangju (KR); Young-Min Woo, Pohang-Shi (KR)

(73) Assignee: Korea Kumho Petrochemical Co., Ltd., Seoul (KR)

( * ) Notice: Subject to any disclaimer, the term of this patent is extended or adjusted under 35 U.S.C. 154(b) by 337 days.

(21) Appl. No.: 11/136,359

(22) Filed: May 25, 2005

(65) Prior Publication Data

US 2006/0272053 A1    Nov. 30, 2006

(51) Int. Cl.
C12N 15/29   (2006.01)
C12N 15/52   (2006.01)
C12N 15/82   (2006.01)
A01H 5/00    (2006.01)
A01H 5/10    (2006.01)

(52) U.S. Cl. .................... 800/320.2; 800/298; 800/287
(58) Field of Classification Search ............. 435/320.1; 536/24.1; 800/282, 287, 298, 320.2
See application file for complete search history.

(56) References Cited

U.S. PATENT DOCUMENTS 6,008,437 A * 12/1999 Krebbers et al. ........... 800/303

OTHER PUBLICATIONS

Shan et al, Yi Chuan Xue Bao. 2000; vol. 27 (1) pp. 65-69 (Abstract only).*
Elio G.W.M. Schijlen et al.: "Modification of flavonoid biosynthesis in crop plants"; Phytochemistry 65(2004) pp. 2631-2648.
B. Winkel-Shirley: Flavonoid Biosynthesis. A Colorful Model for Genetics, Biochemistry, Cell Biology, and Biotechnology; Plant Physiology, Jun. 2001, vol. 126, pp. 485-493.
C. S. Buer et al.: "The transparent testa4 Mutation Prevents Flavonoid synthesis . . . "; The Plant Cell, vol. 16, 1191-1205, May 2004.
R. J. Williams, et al.: "Flavonoids: Antioxidants or Signalling Molecules?"; Free Radical Biology & Medicine, vol. 36, No. 7, pp. 838-849, 2004.
M. I. Yousef, et al.: Antioxidant activities and lipid lowering effects of isoflavone in male rabbits; Food and Chemical Toxicology 42(2004) 1497-1503.
F. Quattrocchio, et al.: Analysis of bHLH and MYB domain proteins: species-specific regulatory differences . . . ; The Plant Journal (1998) 13(4), 475-488.
M.E. Verhoeyen, et al.: Increasing antioxidant levels in tomatoes through modification of the flavonoid biosynthetic pathway; Journal of Experimental Botany, vol. 53, No. 377 pp. 2099-2106, Oct. 2002
F. Quattrocchio, et al.: "Regulatory Genes Controlling Anthocyanin Pigmentation Are Functionally Conserved among Plant Species and Have Distinct Sets of Target Genes" The Plant Cell, vol. 5, 1497-1512, Nov. 1993.

* cited by examiner

Primary Examiner—Russell P. Kallis
(74) Attorney, Agent, or Firm—Kenyon & Kenyon LLP

(57) ABSTRACT

The present invention aims to develop transgenic rice that produces high levels of flavonoids in the entire endosperm. A rice variety, *Oryza sativa japonica* cv. Hwa-Young, is transformed with maize C1 and R-S genes that together activate most structural genes in the flavonoid biosynthetic pathway. Expression of the C1 and R-S transgenes is endosperm-specific for using the promoter of a 13-kD rice prolamin gene that specifically expresses throughout the endosperm. With variation in pigmentation among 27 independent C1/R-S transgenic lines, the T1 kernels of most lines are light brown and apparently darker than kernels of the wild type as well as rice plants transformed with vector alone. The T2 and T3 kernels of homozygous transgenic lines become darker in pigmentation and smaller in size than T1 kernels.

3 Claims, 10 Drawing Sheets

SEQUENCE LISTING

```
<160> NUMBER OF SEQ ID NOS: 15

<210> SEQ ID NO 1
<211> LENGTH: 855
<212> TYPE: DNA
<213> ORGANISM: Maize C1 cDNA

<400> SEQUENCE: 1
gagcttgatc gacgagagag cgagcgcgat ggggaggagg gcgtgttgcg cgaaggaagg      60
cgttaagaga ggggcgtgga cgagcaagga ggacgatgcc ttggccgcct acgtcaaggc     120
ccatggcgaa ggcaaatgga gggaagtgcc ccagaaagcc ggtttgcgtc ggtgcggcaa     180
gagctgccgg ctgcggtggc tgaactacac atcaggcgcg gcaacatctc ctacgacgag     240
gaggatctca tcatccgcct ccacaggctc ctcggcaaca ggtggtcgct gattgcaggc     300
aggctgcctg gccgaacaga caatgaaatc aagaactact ggaacagcac gctgggccgg     360
agggcaggcg ccggcgccgg cgccggcggc agctgggtcg tcgtcgcgcc ggacaccggc     420
tcgcacgcca ccccggccgc gacgtcgggc gcctgcgaga ccggccagaa tagcgccgct     480
catcgcgcgg accccgactc agccgggacg acgacgacct cggcggcggc ggtgtgggcg     540
cccaaggcct gcggtgcac gggcggactc ttcttcttcc accgggacac gacgccggcg     600
cacgcgggcg agacggcgac gccaatgcc ggtggaggtg gaggaggagg aggagaagca     660
```

```
gggtcgtcgg acgactgcag ctcggcggcg tcggtatcgc ttcgcgtcgg aagccacgac      720
gagccgtgct tctccggcga cggtgacggc gactggatgg acgacgtgag ggccctggcg      780
tcgtttctcg agtccgacga ggactggctc cgctgtcaga cggccgggca gcttgcgtag      840
acaacaagta cacgt                                                      855

<210> SEQ ID NO 2
<211> LENGTH: 1863
<212> TYPE: DNA
<213> ORGANISM: Maize R-S cDNA

<400> SEQUENCE: 2
ttcagcaggc gcgtgatggc cgtttcagct tcccgagttc agcaggcgga agaactgctg       60
caacgacctg ctgagaggca gctgatgagg agccagcttg ctgcagccgc caggagcatc      120
aactggagct acgccctctt ctggtccatt tcagacactc aaccaggggt gctgacgtgg      180
acggacgggt tctacaacgg cgaggtgaag acgcggaaga tctccaactc cgtggagctg      240
acatccgacc agctcgtcat gcagaggagc gaccagctcc gggagctcta cgaggccctc      300
ctgtcgggcg agggcgaccg ccgcgctgcg cctgcgcggc cggccggctc tctgtcgccg      360
gaggacctcg gcgacaccga gtggtactac gtggtctcca tgacctacgc cttccggcca      420
ggccaagggt gcccggcag gagtttcgcg agcgacgagc atgtctggct gtgcaacgcg      480
cacctcgccg gcagcaaagc cttccccgc gcgctcctgg ccaagagcgc gtccattcag      540
tcaatcctct gcatcccggt tatgggcggc gtgcttgagc ttggtacaac tgacacggtg      600
ccggaggccc cggacttggt cagccgagca accgcagctt tctgggagcc gcagtgcccg      660
acgtactcgg aagagccgag ctccagcccg tcaggacgag caaacgagac cggcgaggcc      720
gcagcagacg acggcacgtt tgcgttcgag gaactcgacc acaataatgg catggacata      780
gaggcgatga ccgccgccgg gggacacggg caggaggagg agctaagact aagagaagcc      840
gaggccctgt cagacgacgc aagcctggag cacatcacca aggagatcga ggagttctac      900
agcctctgcg acgaaatgga cctgcaggcg ctaccactac cgctagagga cggctggacc      960
gtggacgcgt ccaatttcga ggtcccctgc tcttccccgc agccagcgcc gcctccggtg     1020
gacagggcta ccgctaacgt cgccgccgac gcctcaaggg cgcccgtcta cggctctcgc     1080
gcgaccagtt tcatggcttg gacgaggtcc tcgcagcagt cgtcgtgctc cgacgacgcg     1140
gcgccggcag tagtgccggc catcgaggag ccgcagagat tgctgaagaa agtggtggcc     1200
ggcggcggtg cttgggagag ctgtggcggc gcgacggaga cagcacagga aatgagtgcc     1260
accaagaacc acgtcatgtc ggagcgaaag cgacgagaga agctcaacga atgttcctc     1320 gtcctcaagt cactgcttcc gtccattcac agggtgaaca aagcgtcgat cctcgccgaa     1380
acgatagcct acctcaagga gcttcagcga agggtgcaag agctggagtc cagtagggaa     1440
cctgcgtcgc gcccatccga aacgacgaca aggctaataa caaggccctc ccgtggcaat     1500
aatgagagtg tgaggaagga agtctgcgcg ggctccaaga ggaagagccc agagctcggc     1560
agagacgacg tggagcgccc cccggtcctc accatggacg ccggctccag caacgtcacc     1620
gtcaccgtct cggacaagga cgtgctcctg gaggtgcagt gccggtggga ggagctcctg     1680
atgacgcgag tgttcgacgc catcaagagc ctccatttgg acgtcctctc ggttcaggct     1740
tcagcgccag atggcttcat ggggcttaag atacgagctc agtttgctgg ctccggtgcc     1800
gtcgtgccct ggatgatcag cgaggctctt cgcaaagcta tagggaagcg gtgaagggc     1860 agc                                                                  1863
```

<210> SEQ ID NO 3
<211> LENGTH: 638
<212> TYPE: DNA
<213> ORGANISM: Oryza sativa

<400> SEQUENCE: 3

| | | | | |
|---|---|---|---|---|
| ggtgtagcaa | cacgacttta | ttattattat | tattattatt | attattattt | tacaaaaata | 60 |
| taaaatagat | cagtccctca | ccacaagtag | agcaagttgg | tgagttattg | taaagttcta | 120 |
| caaagctaat | ttaaaagtta | ttgcattaac | ttatttcata | ttacaaacaa | gagtgtcaat | 180 |
| ggaacaatga | aaaccatatg | acatactata | attttgtttt | tattattgaa | attatataat | 240 |
| tcaaagagaa | taaatccaca | tagccgtaaa | gttctacatg | tggtgcatta | ccaaaatata | 300 |
| tatagcttac | aaaacatgac | aggcttagtt | tgaaaaattg | caatccttat | cacattgaca | 360 |
| cataaagtga | gtgatgagtc | ataatattat | tttctttgct | acccatcatg | tatatatgat | 420 |
| agccacaaag | ttactttgat | gatgatatca | agaacatttt | taggtgcac  | ctaacagaat | 480 |
| atccaaataa | tatgactcac | ttagatcata | atagagcatc | aagtaaaact | aacactctaa | 540 |
| agcaaccgat | gggaaagcat | ctataaatag | acaagcacaa | tgaaaatcct | catcatcctt | 600 |
| caccacaatt | caaatattat | agttgaagca | tagtagta   |            |            | 638 |

<210> SEQ ID NO 4
<211> LENGTH: 33
<212> TYPE: DNA
<213> ORGANISM: Artificial Sequence
<220> FEATURE:
<223> OTHER INFORMATION: Primer

<400> SEQUENCE: 4
attctagacg agcttgatcg acgagagagc gag         33

<210> SEQ ID NO 5
<211> LENGTH: 32
<212> TYPE: DNA
<213> ORGANISM: Artificial Sequence
<220> FEATURE:
<223> OTHER INFORMATION: Primer

<400> SEQUENCE: 5
cgagctcgac gtgtacttgt tgtctacgca ag          32

<210> SEQ ID NO 6
<211> LENGTH: 28
<212> TYPE: DNA
<213> ORGANISM: Artificial Sequence
<220> FEATURE:
<223> OTHER INFORMATION: Primer

<400> SEQUENCE: 6
gctctagacg ttcagcaggc gcgtgatg              28

<210> SEQ ID NO 7
<211> LENGTH: 31
<212> TYPE: DNA
<213> ORGANISM: Artificial Sequence
<220> FEATURE:
<223> OTHER INFORMATION: Primer

<400> SEQUENCE: 7
cccccggggg ctgcccttc accgcttccc t           31

```
<210> SEQ ID NO 8
<211> LENGTH: 24
<212> TYPE: DNA
<213> ORGANISM: Artificial Sequence
<220> FEATURE:
<223> OTHER INFORMATION: Primer

<400> SEQUENCE: 8
aagcttggtg tagcaacacg actt                                              24

<210> SEQ ID NO 9
<211> LENGTH: 32
<212> TYPE: DNA
<213> ORGANISM: Artificial Sequence
<220> FEATURE:
<223> OTHER INFORMATION: Primer

<400> SEQUENCE: 9
cgggatcccg gatctagtaa catagatgac ac                                     32

<210> SEQ ID NO 10
<211> LENGTH: 24
<212> TYPE: DNA
<213> ORGANISM: Artificial Sequence
<220> FEATURE:
<223> OTHER INFORMATION: Primer

<400> SEQUENCE: 10
ggatccggtg tagcaacacg agtt                                              24

<210> SEQ ID NO 11
<211> LENGTH: 30
<212> TYPE: DNA
<213> ORGANISM: Artificial Sequence
<220> FEATURE:
<223> OTHER INFORMATION: Primer

<400> SEQUENCE: 11
ggaattccga tctagtaaca tagatgacac                                        30

<210> SEQ ID NO 12
<211> LENGTH: 26
<212> TYPE: DNA
<213> ORGANISM: Artificial Sequence
<220> FEATURE:
<223> OTHER INFORMATION: Primer

<400> SEQUENCE: 12
tacatcgaga caagcacggt caactt                                            26

<210> SEQ ID NO 13
<211> LENGTH: 26
<212> TYPE: DNA
<213> ORGANISM: Artificial Sequence
<220> FEATURE:
<223> OTHER INFORMATION: Primer

<400> SEQUENCE: 13
tgccagaaac ccacgtcatg ccagtt                                            26

<210> SEQ ID NO 14
<211> LENGTH: 20
<212> TYPE: DNA
<213> ORGANISM: Artificial Sequence
<220> FEATURE:
<223> OTHER INFORMATION: Primer
```

```
<400> SEQUENCE: 14
aactgggatg atatggagaa                                          20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
cctccaatcc agacactgta                                          20
```

TRANSGENIC RICE LINE PRODUCING HIGH LEVEL OF FLAVONOIDS IN THE ENDOSPERM

BACKGROUND OF THE INVENTION

1. Field of the Invention

This invention relates to a transgenic rice line containing a high level of various flavonoids in kernels of rice. Further, this invention relates to a transgenic rice line transformed with maize C1 and R-S genes.

2. Description of Prior Art

Extensive studies on crop plants have significantly improved productivity through breeding for high yield, disease/pest-resistance, and semi-dwarfism. In recent years, genetic engineering tools along with conventional breeding methods are readily employed to develop new crop varieties with not only improved productivity but also fortified nutritional quality.

One of the well-known examples is the provitamin A-producing "Golden Rice," of which endosperm is genetically engineered with three genes involved in the carotenoid biosynthetic pathway (Ye et al., 2000). Cahoon et al. (2003) reported development of a transgenic corn that produces four to six times more vitamin E in embryos by over-expressing barley homogentisic acid geranylgeranyl transferase.

Over 2,000 flavonoids produced in plants are known to be involved in pigmentation of flowers and fruits, protection against UV and pathogens, signaling to symbiotic microorganisms, and male fertility in some plant species (reviewed in Shirley, 1996; Winkel-Shirley, 2001a, 2001b and 2002). All flavonoids possess the phenylbenzopyrone flavonoid skeleton that is synthesized through sequential condensation reactions of a p-coumaroyl-CoA and three molecules of malonyl-CoA. In addition to subtle modifications of phenylbenzopyrone itself, flavonoids are diversified by addition of various moieties such as hydroxyl, methyl and sugar groups to the basic structure.

Flavonoids have been extensively studied for their biological activities including antioxidant, antiviral, anti-cancer, anti-aging, hepatoprotective effects, cancer prevention, enhancing immune system, and improving serum lipid quality that consequently lowers the risk of cardiovascular disease (Dixon and Steele, 1999; Yousef et al., 2004).

Although most health-beneficial roles are primarily associated with antioxidant property of flavonoids functioning as reducing agents, hydrogen donors, and free radical quenchers; a number of nonantioxidant activities have been also reported for inhibitory effects on carcinogenesis (Jankun et al., 1997; reviewed in Ren et al., 2003) and modulatory effects on receptors and intracellular signaling enzymes (reviewed in William et al., 2004). Pinent et al. (2004) also reported that procyanidins, oligomeric flavonoids, have antidiabetic properties, possibly through interaction with signaling components such as phosphatidylinositol 3-kinase and p38 mitogen-activated protein kinase. As a similar work, Enomoto et al. (2004) demonstrated inhibitory effect of 3-methoxy quercetin on human aldose reductase, platelet aggregation, and blood coagulation.

Among major secondary metabolic pathways in plants, flavonoid biosynthesis is the best characterized one for molecular genetics of the genes and biochemical mechanisms of the enzymes involved in the pathway (reviewed in Holton and Cornish, 1995; Winkel-Shirley, 2001a and 2001b). Members of C1 and R regulatory gene families encoding Myb-type transcription factors and basic helix-loop-helix-type transcription factors, respectively, individually or mutually activate different sets of structural genes in the flavonoid biosynthetic pathway (Quattrocchio et al., 1993; Quattrocchio et al., 1998).

Members of both gene families have been isolated from a number of monocot as well as dicot species and known to be highly conserved within the corresponding families. For this reason, some of the C1 and R family members are functionally interchangeable among different plant species (reviewed in Schijlen et al., 2004). For example, ectopic expression of both maize C1 and R was sufficient to produce anthocyanins in root, petal, and stamen tissues that normally lack anthocyanins in *Arabidopsis* and tobacco (Lloyd et al., 1992). Similarly, Bovy et al. (2002) reported that tomato plants transformed with both maize C1 and LC (a member of R gene family) produced anthocyanins and additional flavonoids in the leaves and in the fruit flesh, respectively. In addition to regulatory genes, enhanced production of specific flavonoids in the specific tissues of tomato fruits was demonstrated by elevated expression of biosynthetic genes for chalcone synthase, chalcone isomerase, and flavonol synthase (Verhoeyen et al., 2002).

SUMMARY OF THE INVENTION

Regular white rice, *Oryza sativa japonica* cv. Hwa-Young, was transformed with maize C1 and R-S regulatory genes each under the control of an endosperm-specific promoter. The T2 and T3 kernels of homozygous transgenic lines, named as "Green Tea rice" (GT rice), became darker in pigmentation and smaller in size than T1 and T2 hemizygous kernels that are, in turn, slightly darker than the untransformed kernels without difference in size.

In addition to expression of C1 and R-S transgenes, genes of the flavonoid biosynthetic pathway activated by C1 and R-S transgenes were confirmed by RT-PCR using RNAs extracted from developing kernels of T3 homozygous lines. Among the activated genes, expression levels of phenylalanine ammonia lyase, chalcone synthase, flavanone 3-hydroxylase, flavonoid 3'-hydroxylase, and dihydroflavonol 4-reductase substantially increased in the GT rice, whereas expression of these genes was hardly detectable in the wild type. The anthocyanidin synthase gene, however, was not activated by the transgenes, that might explain no anthocyanin production in the GT rice kernels.

Comparison of HPLC flavonoid profiles revealed that high levels of various flavonoids are produced in the GT rice kernels. Due to numerous types of flavonoids in the extract of transgenic kernels, it was technically infeasible to identify individual HPLC peaks by matching retention times with those of reference compounds. Furthermore, commercially available flavonoid standards are limited for the HPLC analyses. To circumvent these technical problems, the number of peaks in the HPLC profile was reduced by moderate acid-hydrolysis and ethyl acetate partitioning. Subsequently, the major peaks were further analyzed by using LC/MS/MS and NMR, from which dihydroquercetin (taxifolin), dihydroisorhamnetin (3'-O-methyl taxifolin), and 3'-O-methyl quercetin were identified. Using authentic taxifolin as a reference, the concentrations of taxifolin, 3'-O-methyl taxifolin, 3'-O-methyl quercetin, and total flavonoid content were estimated to 150 µg, 330 µg, 55 µg, and 12 mg per gram of dry kernels, respectively. Fluorescent labeling of flavonoids with diphenylboric acid in T3 GT rice kernels showed that flavonoids are highly concentrated in 4-5 layers of the outer endosperm. More importantly, a moderate level of flavonoids was also detected throughout the inner endosperm.

DETAILED DESCRIPTION OF THE INVENTION

Figure 1:
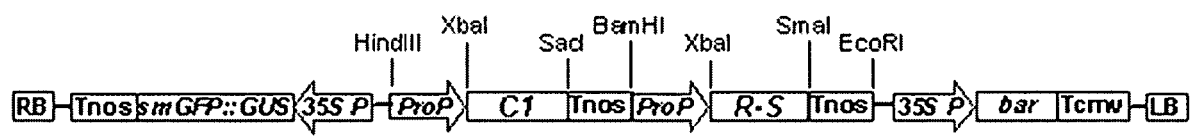
FIG. 1. C1/R-S transgene construct used in the transformation. The construct backbone was derived from a binary vector pCAMBIA3301. RB, T-DNA right border; Tnos, nopaline synthase gene terminator; smGFP::GUS, soluble modified green fluorescent protein gene fused with β-glucuronidase (GUS) coding sequence; 35S P, CaMV 35S promoter; ProP, a rice 13-kD prolamin NPR33 promoter; C1, maize MYB-type transcription factor (accession AF320614); R-S, maize bHLH-type transcription factor (accession X15806); bar, bialaphos-resistant gene; Tcmv, CaMV 35S terminator; LB, T-DNA left border.

We also developed transgenic rice producing flavonoids in the endosperm by ectopically expressing maize C1 and R-S genes with rationale as follows: (1) Regular rice kernels lack flavonoids, whereas "black rice" kernels contain a few kinds of colored flavonoids, anthocyanins, only in the pericarp that is completely removed by milling. (2) Dietary flavonoids have various health-promoting effects such as antioxidant, antiviral, anti-cancer, anti-aging, and hepatoprotective effects, as well as cancer prevention, and enhancing immune system (Dixon and Steele, 1999; reviewed in Ren et al., 2003). In addition, Howitz et al. (2003) suggested that flavonoids function to extend even mammalian lifespan, based on its biological activity to activate genes involved in extending lifespan of yeast. (3) As introduced in the endosperm, C1 and R-S genes are expected to activate most, if not all, of structural enzyme genes in the flavonoid biosynthetic pathway Levels and types of flavonoids vary significantly, depending on not only plant species but also tissue types. For example, endosperms of cereals lack flavonoids, whereas green tea (*Camellia sinensis*) leaves contain high levels of flavonoids accounting for 10-20% of dry weight. For varieties of "black rice", a few types of anthocyanins, colored flavonoids, are produced only in the pericarp. Therefore, we aimed to develop transgenic rice lines in which flavonoids are produced throughout the entire endosperm of kernels. Our strategies include (1) transforming regular japonica rice with maize C1 and R-S (a seed-specific member of R gene family) genes in order to activate various structural genes in the flavonoid biosynthetic pathway and (2) using a endosperm-specific promoter to control expression of the transgenes in order to circumvent side effects on vegetative tissues of transgenic plants.

EXAMPLES

Construction of the C1/R-S transgene

Clones of maize C1 (GenBank accession AF320614) having DNA sequence of SEQ ID NO: 1 and R-S (accession X15806) having DNA sequence of SEQ ID NO: 2 in EcoRI sites of p35SC1 and pBluescript SK, respectively, were given by Dr. Karen Cone at University of Missouri in the United States as a gift. A clone of prolamin NPR33 promoter (a 5' UTR between −652 and −13 from the ATG start site of a rice 13-kD prolamin gene) (SEQ ID NO: 3) in pUC18 plasmid was provided by Dr. Fumio Takaiwa at National Institute of Agrobiological Sciences in Japan as a gift. The promoter was subcloned into the HindIII/XbaI sites of modified pGEM7Zf(+) plasmid (Promega Co., Madison, Wis.) that contains a Nos terminator (Tnos) at SacI/EcoRI sites, designated as pYMPP. C1 cDNA (822 bp) was amplified by PCR using the p35SC1 plasmid containing C1 cDNA as a template, a forward primer with a XbaI restriction site (5'-ATTCTAGACGAGCTTGATCGACGAGAG AGC-GAG-3')(SEQ ID NO: 4), and a reverse primer with a SacI site (5'-CGAGCTCGACGT GTACTTGTTGTCTACG-CAAG-3') (SEQ ID NO: 5). The PCR product was digested with XbaI and SacI and ligated into the same restriction sites of the pYMPP plasmid, designated again as pYMPPC1. Up to this step, R-S cDNA (1839 bp) was subcloned into the pYMPP plasmid in the same way, using a different primer set, 5'-GCTCTAGACGTTCAGCAGGCG CGTGATG-3' (SEQ ID NO: 6) and 5'-CC CCCGGGGGCTGCCCCTTCACCGCTTCCCT-3' (SEQ ID NO: 7) corresponding to the R-S sequence with a XbaI site at the end of forward primer and a SmaI site at the end of reverse primer, designated again as pYMPPR-S. Products of PCR using pYMPPC1 plasmid DNAs as a template, a forward primer for the NPR33 promoter with a Hind III site (5'-AAGCTTGGTGTAGCAACACGACTT-3') (SEQ ID NO: 8), and a reverse primer for Tnos with a BamH I site (5'-CGGGATCCCGGATCTAG TAACATAGATGACAC-3') (SEQ ID NO: 9) were digested with Hind III and BamH I and ligated into the same restriction sites of a modified pCambia3301 binary vector that contains smGFP::GUS as well as phosphinotricin resistant bar gene each under 35S CMV promoter within T-DNA borders. Subsequently, R-S coding sequence with NPR33 promoter and Tnos was amplified by PCR using the pYMPPR-S plasmid DNAs as a template, a forward primer for NPR33 promoter with a BamH I site (5'-GGATCCGGTGTAGCAACACGAGTT-3') (SEQ ID NO: 10), and a reverse primer for Tnos with EcoR I site (5'-GGAATTCCGATCT AGTAACATAGATGACAC-3')(SEQ ID NO: 11). The PCR product was digested with BamH I and EcoR I and ligated into the same restriction sites of the modified pCambia3301 containing C1. The modified pCambia3301 with the coding regions of C1 and R-S genes each having a prolamin NPR33 promoter and a Nos terminator and being fused at a common restriction site BamH I was named as pYMPPC1/R-S and transformed into *Agrobacterium tumefaciens* LBA4404 by the freeze/thaw method.

Rice Transformation

Calli were produced from germinating embryos of *Oryza sativa japonica* cv. Hwa-Young on the callus-inducing medium (N6CI, pH 5.8) containing N6 basal salts and vitamins, 1 g/L of casamino acid, 30 g/L of sucrose, and 2 mg/L of 2,4-D and solidified by 2 g/L of gelite. Within 1 or 2 weeks after subculture on fresh medium, the calli were infected with *Agrobacterium tumefaciens* LBA4404 harboring the binary vector pYMprolaminProC1/R-S and co-cultured with the *Agrobacterium* on the N6CI medium supplemented with 100 M acetosyringone in the dark for 3 days at 25° C. Transformed callus cells were selected by culturing for about 3 weeks on a selection medium consisting of N6 basal salts and vitamins, 1 g/L of casamino acid, 30 g/L of sucrose, 2 mg/L of 2,4-D, 500 mg/L of carbenicillin, and 6 mg/L of phosphinotricin. Subsequently, the calli were transferred to a pre-regeneration medium containing N6 basal salts and vitamins, 2 g/L of casamino acid, 30 g/L of sucrose, 30 g/L of sorbitol, 1 mg/L of 2,4-D, 0.5 mg/L of 6-benzyladenine, 0.25 g/L of cefataxime, and 6 mg/L of phosphinotricin. After 10 days of culture on the pre-regeneration medium, the calli were transferred to a regeneration medium (MS basal salts and vitamins, 2 g/L of casamino acid, 30 g/L of sucrose, 20 g/L of sorbitol, 1 mg/L of naphthaleneacetic acid, 5 mg/L of kinetin, 0.125 mg/L of cefortaxime, and 6 mg/L of phosphinotricin). After about 4 weeks on the regeneration medium, greening of calli and regenerated plantlets from the calli were apparent. Regenerated plantlets were transferred to a growth medium (MS basal salts and vitamins, 30 g/L of sucrose, 3 g/L of gelite, pH 5.8) and grown to about 10 cm-tall prior to transfer to soil.

GUS Analysis

After T0 plants were grown for about a month, 3-4 leaf discs were punched out from each plant and incubated in GUS assay solution consisted of 2 mM 5-bromo-4-chloro-3-indole-B-D glucuronide, 1% dimethylformamide, 0.1 mM potassium ferricyanide, 0.1 mM potassium ferrocyanide, and 1 mM EDTA in 500 mM sodium phosphate buffer, pH 7.0 for 18 hrs. Subsequently, the leaf discs were washed in 70% ethanol for 1 hr and then in 100% ethanol for up to 48 hrs in order to completely remove chlorophylls.

Genomic DNA Isolation and Genomic DNA PCR to Verify Transgene Integration

About 2 g of leaf tissues was ground in liquid nitrogen to fine powder and homogenized in 9 mL of the extraction solution consisted of 1% cetyltrimethylammonium bromide (w/v), 1% β-mercaptoethanol (v/v), 700 mM NaCl, and 10 mM EDTA in 100 mM Tris-HCl buffer (pH 7.5). The homogenate was incubated at 65° C. for 1-1.5 hrs with shaking every 15 min. After cooling down, 5 mL of chloroform/isoamyl alcohol (24:1) was added and gently shaken for 5 min. The mixture was centrifuged at 3,000 rpm for 10 min, and the supernatant was transferred to a new 15 mL Falcone tube. The extract was treated with RNase A at a final concentration of 40-50 µg/mL at 35° C. for 30 min. Genomic DNAs were precipitated by adding 6 mL of cold isopropanol and centrifuging at 4,000 rpm for 5 min. The DNA pellet was transferred to a 1.5 mL microfuge tube and washed twice in 0.5 mL of 70% ethanol. The pellet was briefly air-dried and resuspended in 1 mL of nuclease-free water. PCR products were amplified by using about 100 ng of genomic DNAs as templates and a primer set of the bar gene, 5'-TACATCGAGACAAGCACGGTCAACTT-3' (SEQ ID NO: 12) and 5'-TGCCAGAAACCCACGTCATGCCAGTT-3' (SEQ ID NO: 13).

RNA Isolation and RT-PCR to Determine Expression of Transgenes and Genes Involved in Flavonoid Biosynthetic Pathway Total RNAs were isolated from the kernels of T3 homozygous lines at 10 to 15 days after pollination, based on the protocol of "Purification of RNA from cells and tissues by acid phenol-guanidinium thiocyanate-chloroform extraction" in Sambrook and Russell (2001) with minor modifications. The first strand cDNAs of purified total RNAs were synthesized in a total volume of 25 μL containing 3 μg of total RNAs, 1.5 μg of oligo dT, and 200 units of M-MLV reverse transcriptase at 42° C. for 60 min. Relative concentrations of RNAs in different samples were estimated by second PCRs using a primer set of rice actin, 5'-AACTGG-GATGATATGGAGAA-3' (SEQ ID NO: 14) and 5'-CCTC-CAATCCAGACACT GTA-3' (SEQ ID NO: 15). Relative expression levels of C1 and R-S transgenes as well as most genes in flavonoid biosynthetic pathway were determined by second PCRs using the same batches of the first strand cDNAs.

Extraction of Flavonoids from Rice Kernels and HPLC Analysis

Flavonoids were extracted from 1 g of the fine powder of T3 GT rice kernels in 10 mL of 70% methanol by processing through 2 min of vigorous vortexing, 30 min of sonication, and incubation with shaking either for 3 hrs at RT or overnight at 4° C. After the mixture was centrifuged for 10 min at 3,000 rpm, the supernatant was taken and filtered through a 0.45 μm syringe filter. After partitioning with 20 mL of n-hexane to remove lipids, 0.5 mL aliquots of the extract were vacuum-dried for 2 hrs at RT. A dried aliquot was resuspended in 100 μL of 10% methanol, and 20 μL was injected to a Waters™ 600 series HPLC system (Milford, Mass., USA) equipped with a Waters™ Symmetry C18 guard column, a Waters™ XTerra Phenyl column (250 mm×4.6 mm i.d.), and a Waters™ 996 photodiode array detector. The binary mobile phase consisted of 6% acetic acid in 2 mM sodium acetate (final pH 2.5, v/v, solvent A) and 25% solvent A in acetonitrile (v/v, solvent B). HPLC flow rate was 1 mL/min with a gradient running program of 100% solvent A for 10 min, 0-50% solvent B for 40 min, and 50-100% solvent B for 5 min. Data was acquired and processed by using the software Waters™ Millennium 32.

For moderate acid-hydrolysis and ethyl acetate partitioning, each dried aliquot of 0.5 mL extract was dissolved in 100 μL of 1 N HCl containing 0.1% ascorbic acid (w/v) and treated for 10 min at 90° C. To purify aglycones of flavonoids, three volumes of ethyl acetate were added to the acid-hydrolyzed mixture and briefly vortexed. The ethyl acetate phase (the upper phase) was taken and vacuum-dried. Two aliquots were dissolved in 100 μL of 10% methanol for injection into the HPLC system.

Liquid Chromatography Coupled with Electrospray Ionization/Mass Spectrometry

A Finnigan Surveyor™ Modular HPLC System (Thermo Electron Co., USA) with a Waters™ XTerra MS C18 (5 μm, 2.1 mm×150 mm) and a Finnigan LCQ Advantage MAX ion trap mass spectrometer (Thermo Electron Co., USA) equipped with a Finnigan electrospray source were used for individual flavonoid separation and electrospray ionization mass spectrometry, respectively. The systems were operated under the software Xcalibur (version 1.3 SP2, Thermo Electron). HPLC mobile phase consisted of water (solvent A) and acetonitrile (solvent B), both containing 0.1% formic acid. HPLC was run at a flow rate of 0.2 mL/min with a gradient program as follows: 0-3 min, 5% solvent B; 3-50 min, 5-50% solvent B; 50-55 min, 50-100% solvent B; and 55-75 min, 100% solvent B. Mass spectrometry was performed with an electrospray ionization source and the following conditions: 5 kV of spray needle voltage, 200° C. of ion transfer capillary temperature, 60 arbitrary units of nitrogen sheath gas flow rate, and 5 arbitrary units of auxiliary gas flow rate. Full-scan mass spectra were obtained in the range of 100-1000 m/z with 3 microscans and 200 ms of a maximum ion injection time. Data were acquired in positive and negative modes of the LCQ mass spectrometers and by using a software provided with the system.

NMR Determination of Flavonoids Isolated from the T3 Kernels of C1/R-S Transgenic Rice One to three mg of individual flavonoids isolated from the HPLC was dissolved in 0.15 mL of $CD_3OD$. Each sample was transferred to a 3 mm-diameter NMR tube, and its $^1H$ and $^{13}C$ NMR spectra were measured by using a Varian Unity Plus 500 (Walnut Creek, Calif., USA) at 500 MHz and 125 MHz, respectively. NMR gHSQC, gCOSY, and gHMBC pulse sequences were used to determine chemical structures of the isolated flavonoids.

Fluorescent Labeling of Flavonoids in Rice Kernels

Kernels of the wild type and T3 C1/R-S transgenic rice at 25 days after pollination were fixed in 3.7% paraformaldehyde and 0.2% picric acid in 50 mM potassium/5 mM EGTA buffer (pH 6.8). After washing away the fixative in the same buffer, the samples were dehydrated and subsequently infiltrated with paraffin. The paraffin-embedded tissue blocks were sectioned at a thickness of 30 μm. The thin sections were dewaxed, rehydrated, and labeled with saturated (0.25%, w/v) diphenylboric acid (DPBA) for 5 min. The DPBA-labeled sections were examined with an epifluorescence microscope (Olympus BX 51). Fluorescent images were acquired with a FITC filter set by using an Olympus digital camera installed on the microscope.

Color Reaction Assays of the Extract of GT Rice Kernels with Vanillin and DMACA

Working solution of 1% vanillin was prepared by dissolving 0.1 g of vanillin in 10 mL of 5 N HCl, whereas 5% dimethylaminocinnamaldehyde (DMACA) was prepared in methanol containing 5% $H_2SO_4$. Lyophilized extract for 100 mg of dry kernels was dissolved in 0.5 mL of vanillin or DMACA working solutions. Taxifolin and catechin each at a concentration of 100 ppm were used as reference compounds for color reactions. Because vanillin is catechin-specific and produces bright red color, no color is developed when it reacts with taxifolin. DMACA reacting with catechin produces dark greenish blue color, whereas reacting with taxifolin produces purple color.

Results

Production of Transgenic Rice Lines Expressing Maize C1 and R-S Transgenes

Figure 2:
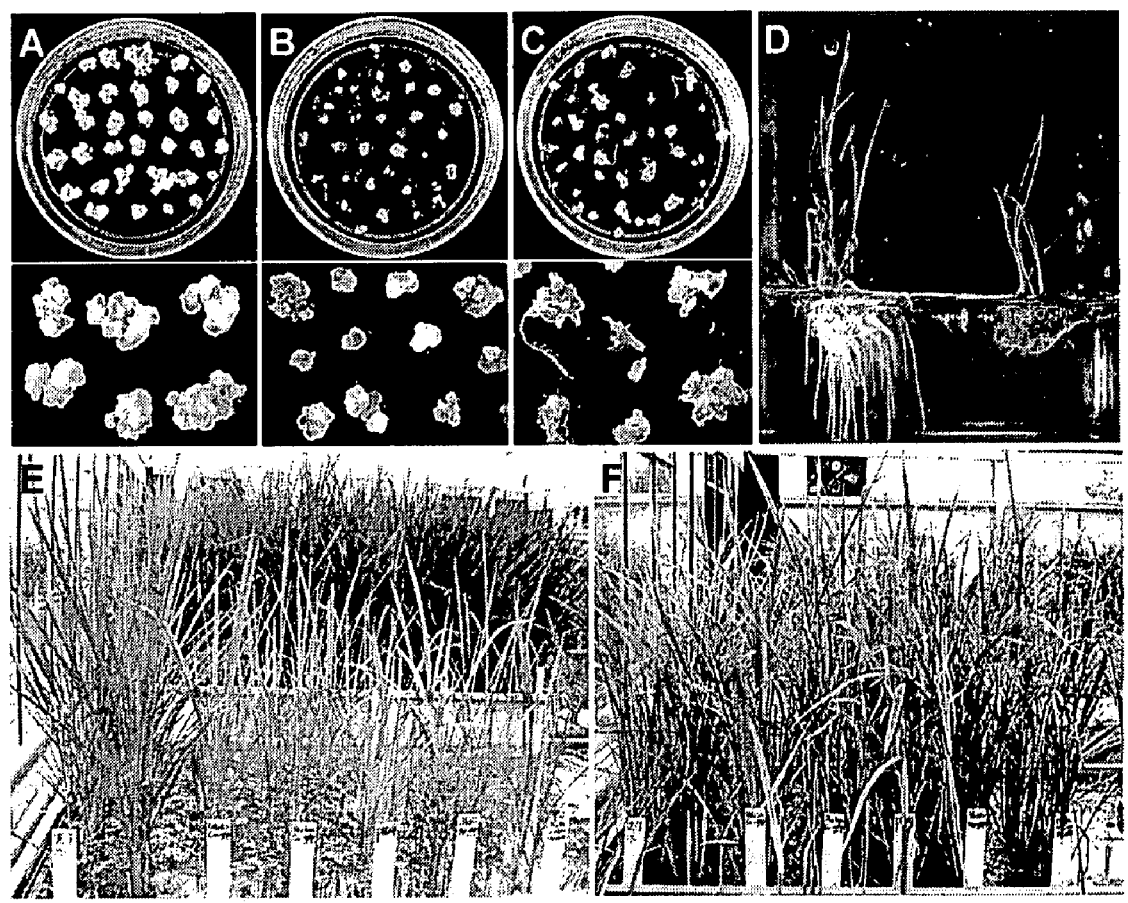
FIG. 2. Production of transgenic rice lines transformed with the maize C1 and R-S transgenes.
(A) Calli induced from germinating embryos of *Oryza sativa japonica* cv. Hwa-Young
(B) Calli infected with *Agrobacterium tumefaciens* LBA4404 harboring the transgenes on basta-containing selection medium
(C) Calli with regenerating plantlets
(D) Regenerated seedlings that are transferred to a magenta box containing MS medium
(E) Transgenic plants that are transferred to the soil in the greenhouse
(F) Mature T0 transgenic plants with panicles FIG. 3. Images of ethidium bromide-stained products of genomic PCR and RT-PCR to confirm presence of the transgene in the genome and to determine relative expression levels of C1 and R-S transgenes in developing transgenic kernels, respectively. The arrows indicate the 1 kb band of DNA size ladder.
(A) Using bar gene primers, PCR products were amplified for genomic DNAs isolated from transgenic lines, 1, 2, 3, 4, 6, 9, and 19. Plasmid DNAs (PL) containing the transgenes were included as a PCR positive control, whereas the wild type genomic DNAs (WT) for a negative control.
(B) RT-PCR products show relative expression levels of C1 and R-S transgenes in the developing kernels of the wild type (WT), 2-1, 4-1, and 9-2 T2 transgenic lines.
Figure 3:
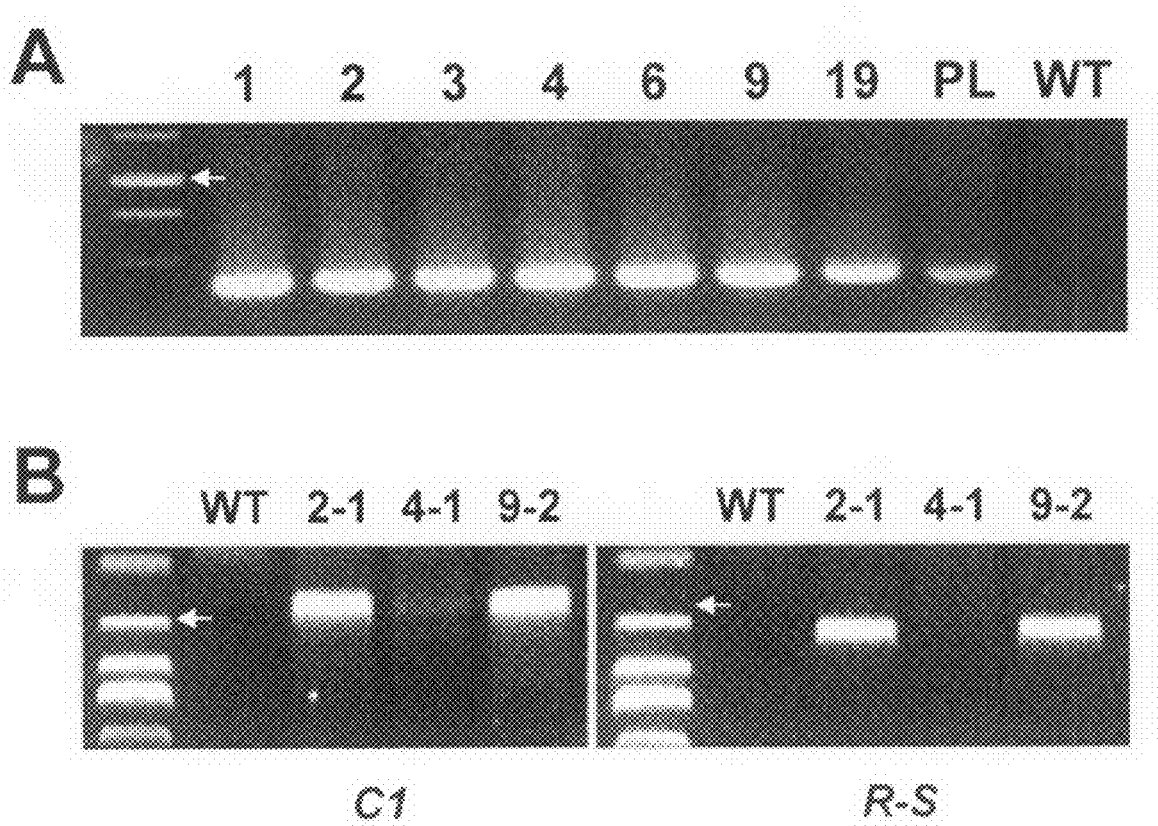

In two separate transformation events, calli induced from germinating embryos of Oryza sativa japonica cv. Hwa-Young were infected with Agrobacterium tumefaciens LBA4404 harboring the C1/R-S transgenes (FIG. 1). Through selection and regeneration of the infected calli, total 27 independent primary transgenic plants (T0) were produced and grown to maturity in a greenhouse (FIG. 2). Presence of the transgenes in the regenerated plants was conveniently determined by either GUS assays or genomic PCRs for the bar gene (FIG. 3A). Germination of T1 kernels on agar plates containing 4 mg/L of phosphinotricin indicated most lines with a single copy of the transgenes, except a few lines possibly with two linked copies. T2 kernels harvested from the herbicide-resistant T1 plants showed no difference in germination and plant growth, compared to the wild type. However, development, particularly dehydration, of T2 kernels was notably delayed, so that T2 kernels on the panicles stayed fresh and soft up to two times longer than the wild type kernels. Growing the T2 plants in a greenhouse during winter rather than summer resulted in production of thin and light kernels, indicating that grain filling was more adversely affected by poor growing conditions in the transgenic lines than in the wild type. A few homozygous transgenic lines of which all T2 kernels exhibited herbicide-resistant were selected, and their T3 kernels were subjected to further analyses.

Various Flavonoids are Produced in the Kernels of GT Rice

Figure 4:
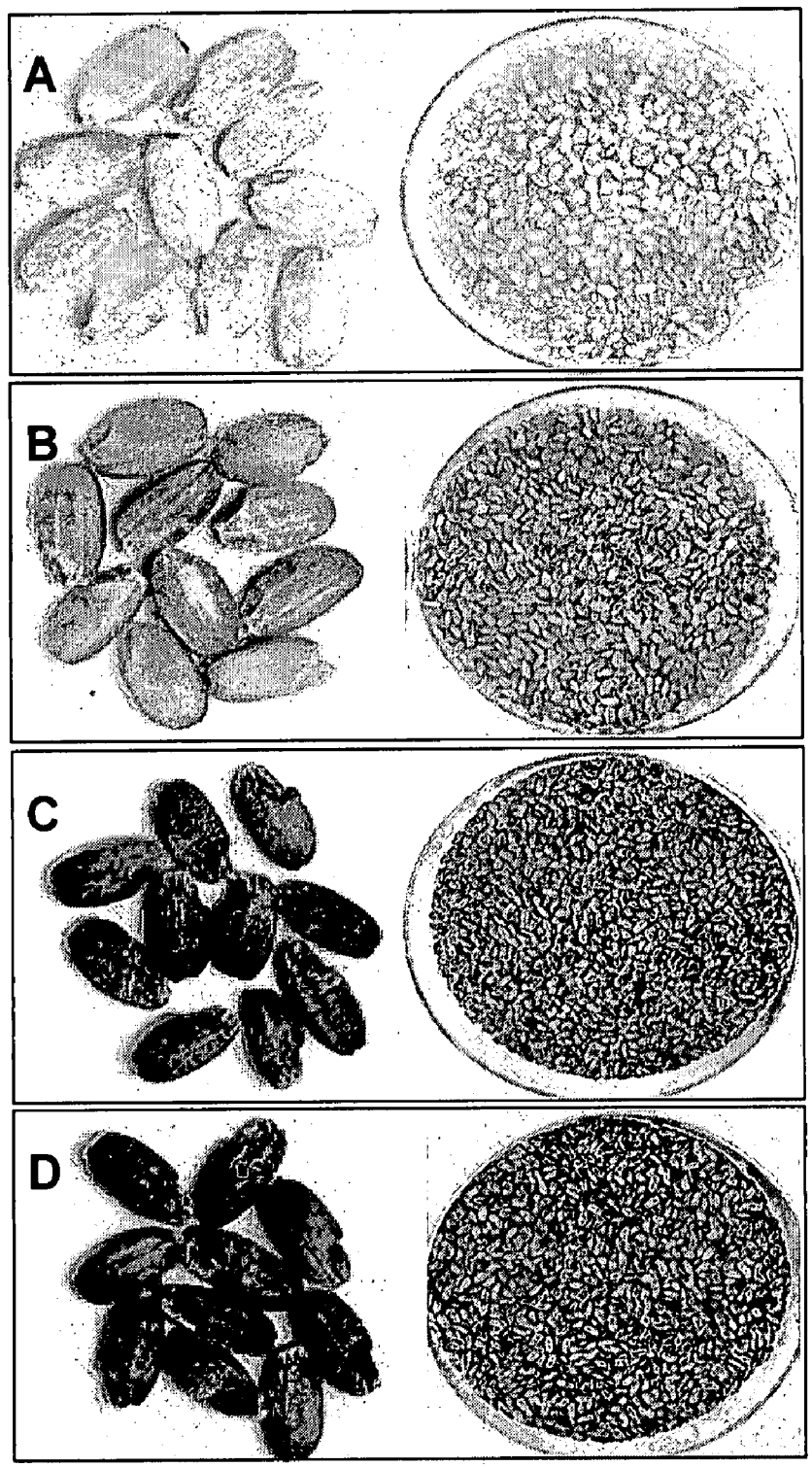
FIG. 4. Comparison of the untransformed, T1, T2, and T3 rice kernels. The T2 (C) and T3 (D) homozygous transgenic kernels are darker in pigmentation and smaller in size than the untransformed (A) and T0 hemizygous transgenic (B) rice kernels.
Figure 5:
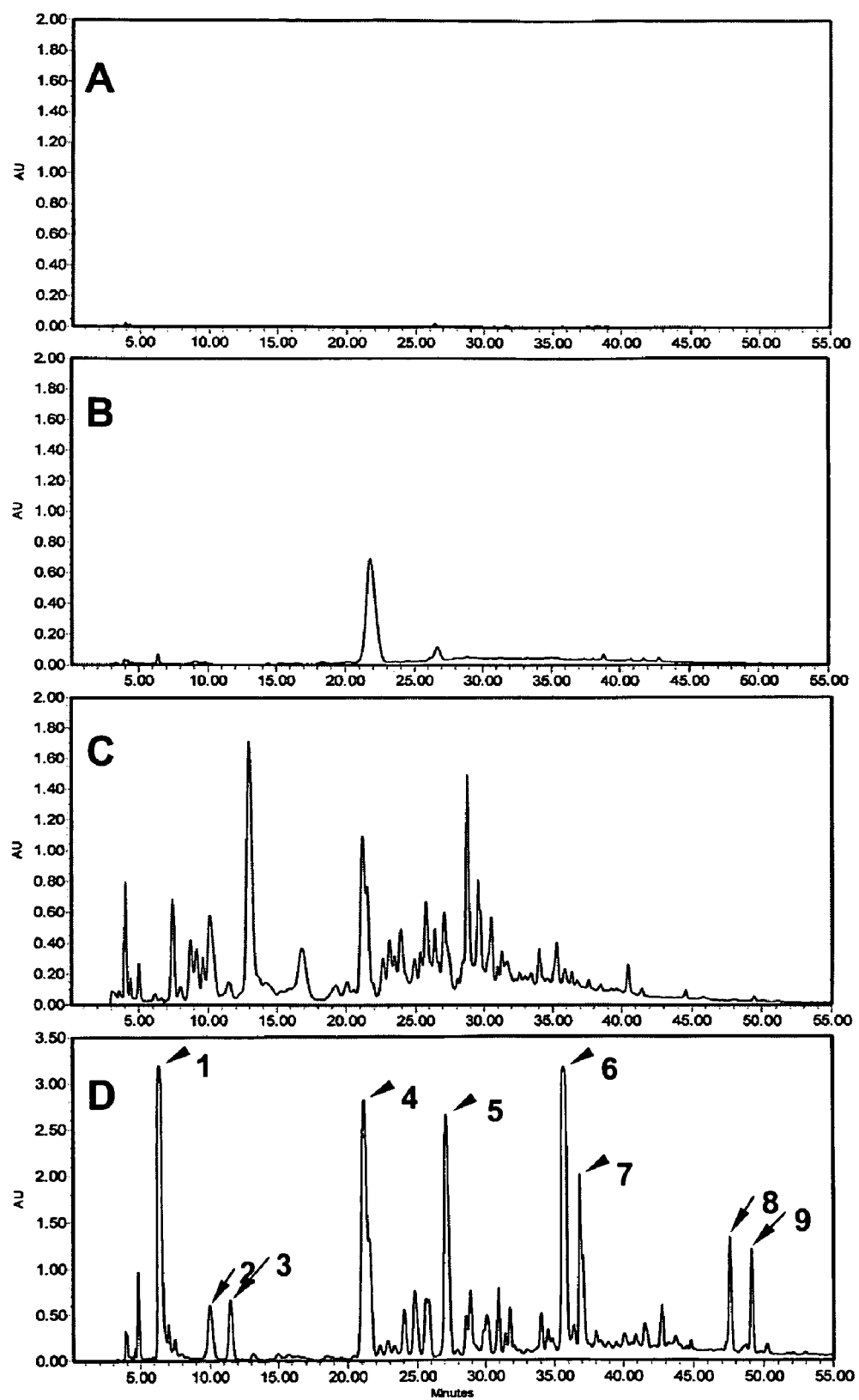
FIG. 5. HPLC profiles of flavonoids extracted from kernels of the Hwa-Young wild type (A), existing black rice Mil-Yang 188 Ho (B), and T3 GT rice (C) without acid hydrolysis and ethyl acetate partition. (D) A HPLC profile of flavonoids extracted from T3 GT rice kernels with subsequent acid hydrolysis and ethyl acetate partition. Minutes, retention times; AU, absorption units.
Figure 6:
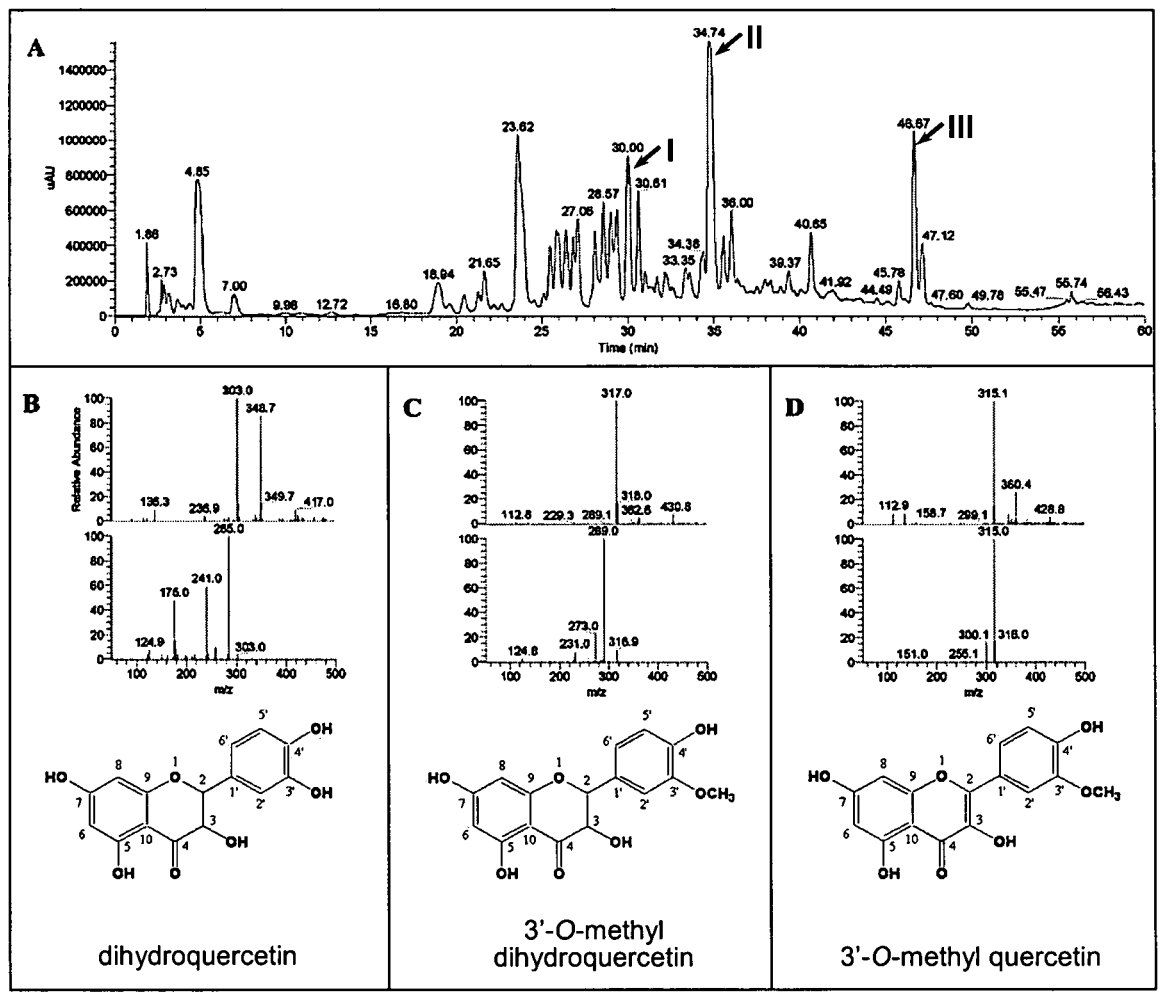
FIG. 6. LC/MS/MS analyses of the flavonoid extract of T3 GT rice kernels and the chemical formula identified by NMR analyses.
(A) A LC chromatogram of the extract that is acid-hydrolyzed and ethyl acetate-partitioned.
(B-D) MS/MS spectra for the compounds I (B), II (C), and III (D) in (A). Chemical formula identified by NMR analyses are shown under the MS/MS spectrum of each compound.

The T2 and T3 kernels of homozygous transgenic lines became darker in pigmentation and smaller in size than T1 kernels that were, in turn, slightly darker than the untransformed kernels (FIG. 4). Expression of the transgenes was estimated by RT-PCRs using RNAs isolated from developing kernels of homozygous lines and primer sets specific for maize C1 and R-S genes. Although RT-PCRs were carried out for more number of transgenic lines, representative images are shown in FIG. 3B. The amounts of RT-PCR products as relative levels of expression ranged from hardly detectable as in the line 4-1 to high levels as in the lines 2-1 and 9-2. However, the C1 and R-S transgenes in each line expressed at quite similar levels. Flavonoids were extracted from kernels of the Hwa-Young wild type, a black rice cultivar Mil-Yang 188 Ho, and a homozygous GT rice in the same manner. HPLC profiles of the extracts without further processes apparently demonstrated that kernels of the GT rice contain a variety of flavonoids at various levels (FIG. 5). In contrast, no flavonoid was detected in the extract of wild type kernels, whereas only a few flavonoids, presumably anthocyanins were found in the black rice. Due to numerous types of flavonoids produced in the GT rice, it was technically infeasible to identify the individual HPLC peaks based on retention times matched with those of reference compounds. Furthermore, commercially available flavonoid standards are limited for the HPLC analysis. To circumvent such technical problems, the kernel extracts were hydrolyzed by acidic condition and subsequently partitioned with ethyl acetate. Consequently, the number of peaks in the HPLC profile was reduced, and, at the same time, levels of some major peaks were significantly increased (FIG. 5D). The m/z values of major peaks determined by LC/MS/MS were used in NMR analyses. Due to limited separation capacity of the HPLC column, the peaks 5, 6, and 8 in the HPLC profile of FIG. 5D corresponding to the peaks I, II, and III in FIG. 6A were accumulated to quantities enough for NMR analysis through up to 12 times of injection of the extract. Based on LC/MS/MS and NMR analyses, the peaks I, II, and III were finally identified as dihydroquercetin (taxifolin), dihydroisorhamnetin (3'-O-methyl taxifolin), and 3'-O-methyl quercetin, respectively (FIG. 6). Using authentic taxifolin as a reference compound and the quantification function of Waters™ Millennium 32 software, amounts of the major compounds were estimated as in Table 1.

TABLE 1

Estimated concentrations of the major peaks of the HPLC profile. Peak#, retention time (RT), and absorption units (AUs) correspond to the HPLC profile of the FIG. 5 (D). Peak# 5, 6, and 8 correspond to the peaks I, II, and III, respectively, in FIG. 6 (A) that are identified by LC/MS/MS and NMR analyses. Concentration μg/g is μg per gram of dry T3 GT rice kernels.

| Peak # | RT(min) | AUs | μg/g |
|---|---|---|---|
| 1 | 6.33 | 3.20 | 268.9 |
| 2 | 9.85 | 0.35 | 29.4 |
| 3 | 11.20 | 0.42 | 35.3 |
| 4 | 20.97 | 2.10 | 176.5 |
| 5 | 26.91 | 1.85 | 155.5 |
| 6 | 35.66 | 3.93 | 330.3 |
| 7 | 36.86 | 1.19 | 100.0 |
| 8 | 47.67 | 0.66 | 55.5 |
| 9 | 49.22 | 0.64 | 53.8 |

Among the nine compounds with widely ranged concentrations, 3'-O-methyl taxifolin of the peak 6 (330.3 μg/g) appeared to be the highest level. Total flavonoid contents in the wild type, existing black rice, T3 GT rice, and green tea leaves were estimated by their $A_{280}$ values of flavonoid extracts in relation to the $A_{280}$ values of known concentrations of taxifolin (Table 2).

TABLE 2

Concentrations of total flavonoids estimated by using taxifolin as a reference at 280 nm wavelength.

| Sample | mg/g dry weight | SD |
|---|---|---|
| Hwa-Young WT | 0.414[a] | 0.0144 |
| Black Rice | 1.900 | 0.0036 |
| C1/R-S T3 | 12.880 | 0.0467 |
| Green Tea | 151.660 | 0.0856 |

SD, standard deviation calculated from 5 measurements per sample.
[a] A low level of flavonoids in the wild type kernels is likely from their embryos.

Figure 7:
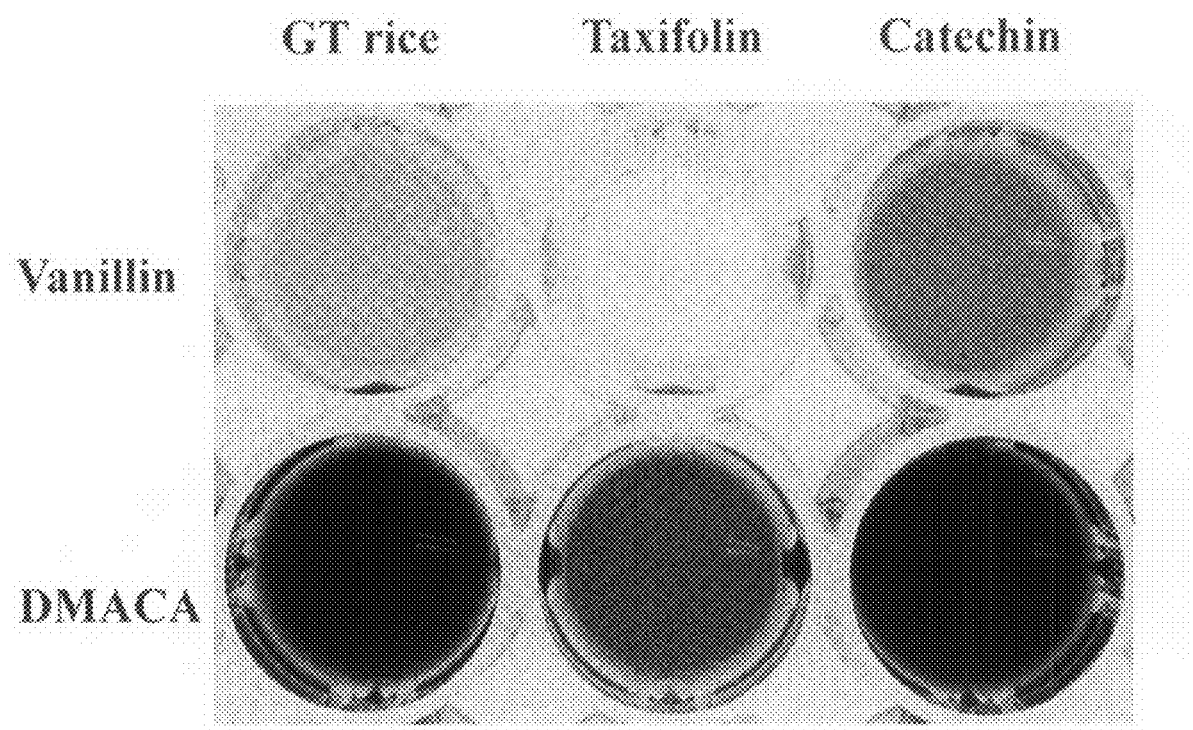
FIG. 7. Color reaction assays of flavonoids. Colors of vanillin- or DMACA-stained extracts of 100 mg dry kernels of T3 GT rice were compared with those of 100 ppm taxifolin and 100 ppm catechin. Vanillin, 1% vanillin in 5 N HCl; DMACA, 0.5% dimethylaminocinnamaldehyde (DMACA) and 5% $H_2SO_4$ in MeOH.

Based on this rough estimation, total flavonoid content in the GT rice was, at least, 30 times and 6 times more than in the wild type and the existing black rice, respectively. However, the GT rice contained about one tenth of total flavonoid content of the compared green tea leaves. About 15% of total flavonoid content in the dried green tea leaves indicated that the quantification system seems to be reasonable, because it falls into the range between 10 to 20%, commonly reported by the other groups. The sum of the major compounds in Table 1 was approximately 1.2 mg/g, accounting for about 1/10 of the estimated total flavonoids in the GT rice kernels. In order to test whether the flavonoid extracts of GT rice contain catechins and catechin derivatives, catechin-specific dye, vanillin, was used for color reaction. Although catechin at a concentration of 100 ppm reacted with vanillin to give a bright red color, the extract of GT rice showed no reaction with vanillin, suggesting that it lacks catechin-type flavonoids. In contrast, presence of taxifolin-type flavonoids in the GT rice was confirmed by DMACA color assay (FIG. 7).

Flavonoid Biosynthetic Pathway Genes Activated by the C1/R-S Transgenes

Figure 8:
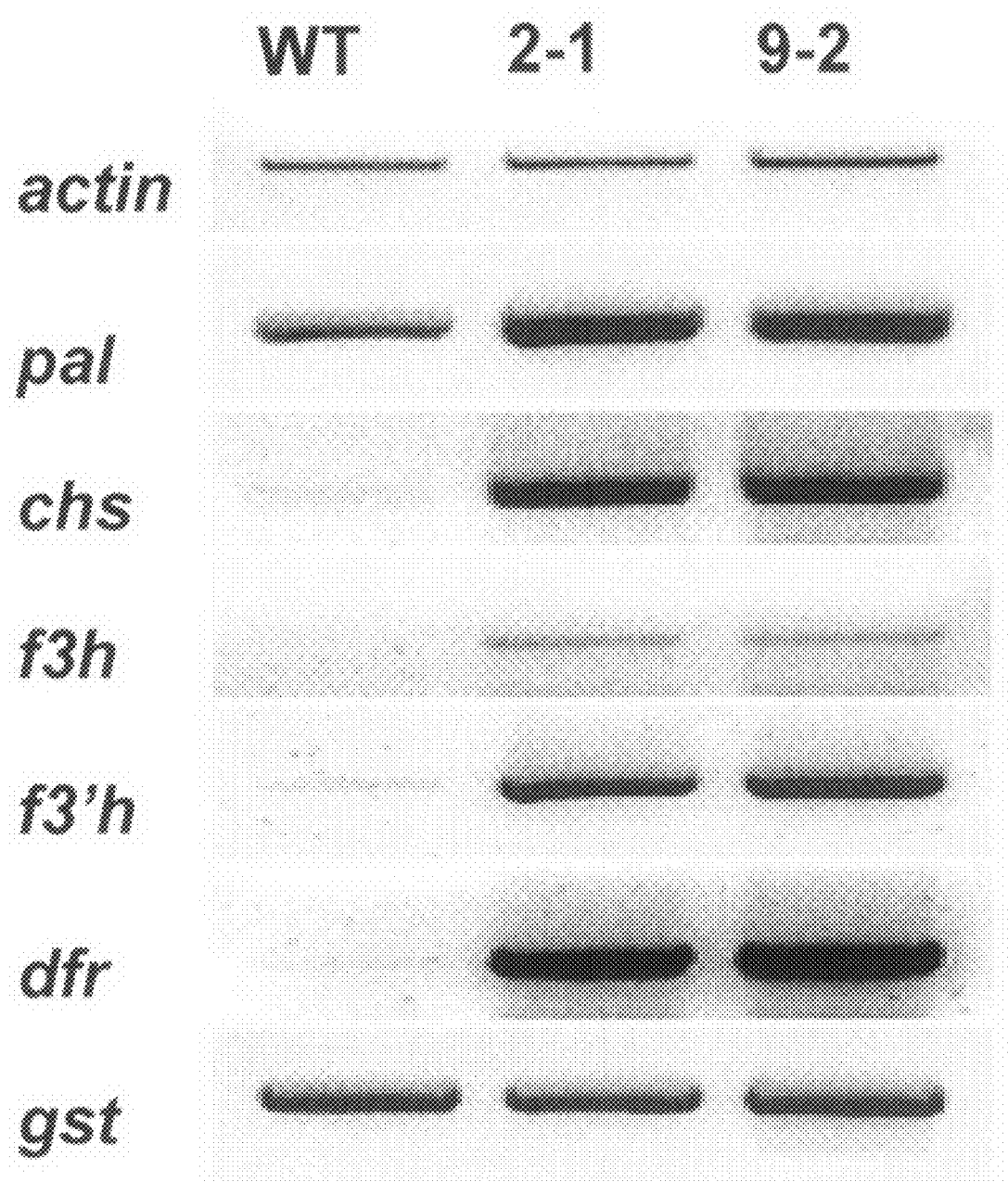
FIG. 8. RT-PCR for flavonoid biosynthetic pathway genes using RNAs extracted from developing kernels of the wild type (WT) and GT rice homozygous lines (2-1 and 9-2). actin, used as a reference for PCR template quantity; pal, phenylalanine ammonia lyase; chs, chalcone synthase; f3h, flavanone 3-hydroxylase; f3'h, flavonoid 3'-hydroxylase; dfr, dihydroflavonol 4-reductase; gst, glutathione-S transferase.
Figure 9:
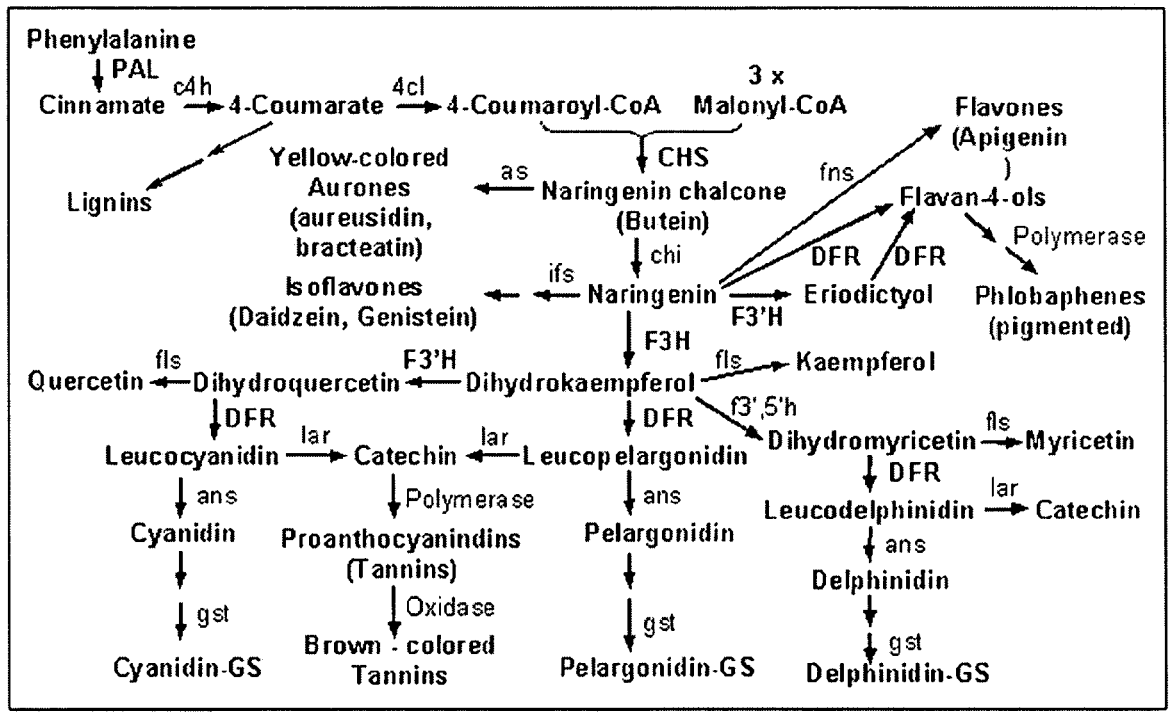
FIG. 9. Flavonoid biosynthetic pathway and the structural genes activated by the C1 and R-S transgenes, that are indicated by bold capital letters. PAL, phenylalanine ammonia lyase; c4h, cinnamate-4-hydroxylase; 4cl, 4 coumarate CoA ligase; CHS, chalcone synthase; chi, chalcone isomerase; fns, flavone synthase; ifs, 2-hydroxyisoflavone synthase; F3H, flavanone 3-hydroxylase; F3'H, flavonoid 3'-hydroxylase; fls, flavonol synthase; DFR, dihydroflavonol 4-reductase; lar, leucoanthocyanidin reductase; ans, anthocyanidin synthase; gst, glutathione-S transferase.

Genes activated by the C1 and R-S transgenes were identified by RT-PCRs using RNAs extracted from developing kernels and primer sets for various genes involved in the flavonoid biosynthetic pathway. The examined genes include phenylalanine ammonia lyase (pal), chalcone synthase (chs), chalcone isomerase (chi), flavone synthase (fns), 2-hydroxyisoflavone synthase (ifs), flavanone 3-hydroxylase (f3h), flavonoid 3'-hydroxylase (f3'h), flavonol synthase (fls), dihydroflavonol 4-reductase (dfr), leucoanthocyanidin reductase (lar), anthocyanidin synthase (ans), and glutathione-S transferase (gst). Among these genes, expressions of pal, chs, f3h, f3'h, and dfr substantially increased in both of the transgenic lines, whereas expressions of these genes were hardly detectable or relatively lower in the wild type (FIG. 8). Due to no activation of lar and ans by the transgenes, the pathway seems to be proceeded up to the biosynthetic step of dihydroflavonols such as dihydrokaempferol and dihydroquercetin (FIG. 9). The results of RT-PCRs were consistent with biochemical analyses of the flavonoids extracted from the GT rice.

Flavonoids are Produced Throughout the Entire Endosperm of GT Rice

Figure 10:
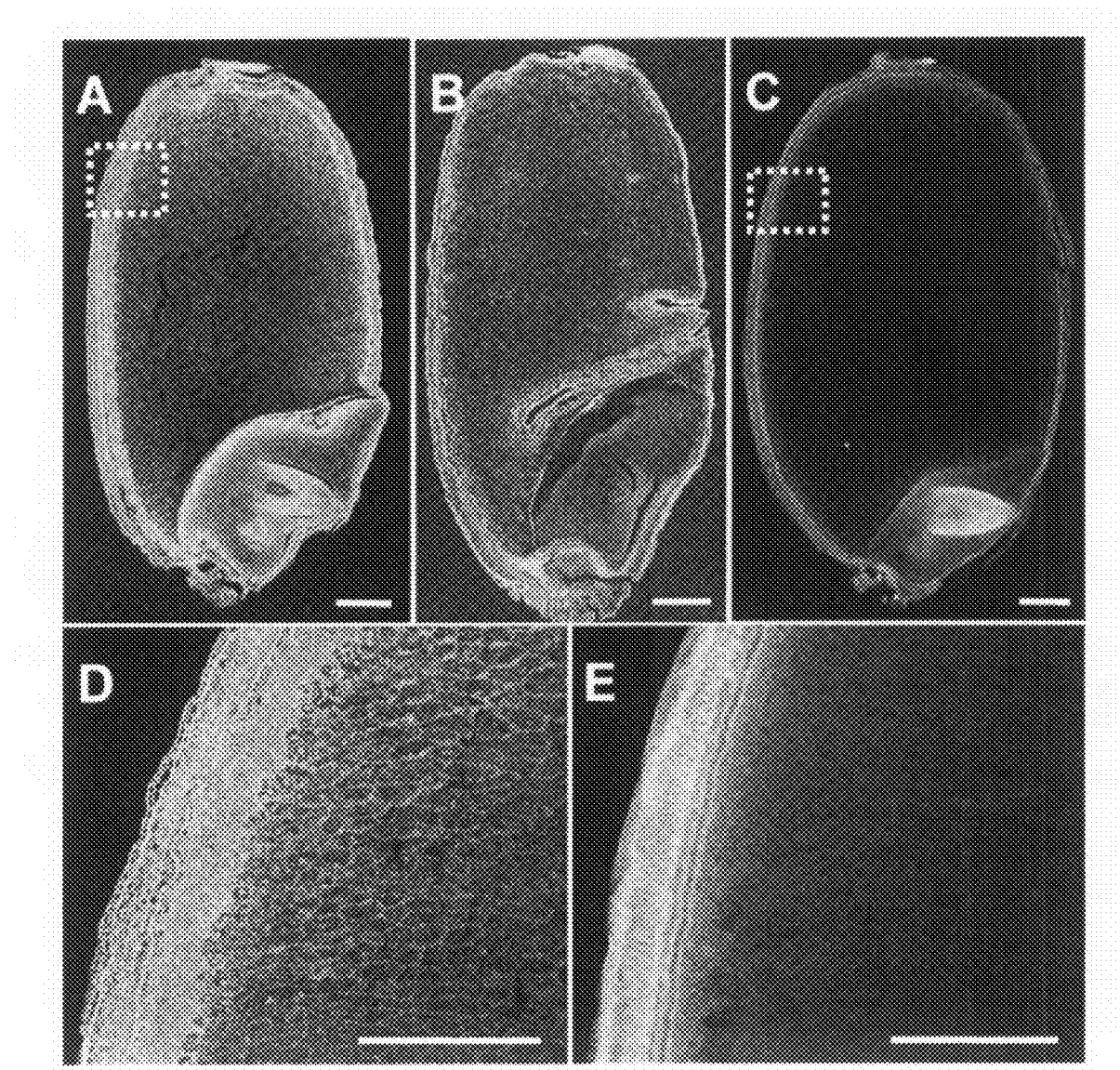
FIG. 10. Sections of T3 GT rice (A, D) and the wild type (C, E) kernels, labeled with diphenylboric acid (DPBA). Labeled flavonoids are depicted as green fluorescent signal. (B) The section of a T3 GT rice kernel without DPBA labeling as a labeling negative control. Signal in the embryo axis of the wild type kernel (C) serves as a labeling positive control. (D) and (E) are the insets of (A) and (C) at a higher magnification, respectively. Scale bars in (A), (B), and (C), 0.5 mm; in (D) and (E), 0.2 mm.

For general labeling of flavonoids, thin sections of the GT rice and the wild type kernels were incubated with saturated diphenylboric acid (DPBA). Microscopy using an epifluorescence microscope with a FITC filter set revealed that DPBA-derived fluorescence level was much higher in the sections of GT rice than in the wild type (FIG. 10). Because DPBA fluoresces only upon binding to flavonoids, the high fluorescence signal in the GT rice kernel indicates presence of high levels of flavonoids. In the labeled section of GT rice kernel, concentrated fluorescence signal in the cell layers of outer endosperm appeared as a thick green fluorescent band (FIG. 10A). At a higher magnification, it was determined that the highly fluorescent band consisted of 4-5 cell layers including the aleurone layer (FIG. 10D). Fluorescence signal abruptly attenuated in the starchy endosperm inner of the highly fluorescent band, probably due to starch granules that limit free cytoplasm and, at the same time, blocks fluorescence signal of DPBA-labeled flavonoids.

Cereals such as maize, wheat, barley, and rice lack flavonoids in the endosperm, while some varieties of cereal species with colored kernels produce a few types of anthocyanins in the pericarp. Production of flavonoids is also limited in the peel of fruits such as apple and tomato.

Since genes involved in flavonoid synthesis are not expressed in the endosperm, introduction of regulatory genes that activate Rice genome has three members of R gene family with about 75% identity to the amino acid sequences of maize R-S and LC transcription factors (Hu et al., 2000). High homology with maize R (Lc) gene. Expression of rice Rb2 gene along with maize C1 gene in maize suspension cells induced production of anthocyanins (Hu et al., 2000).

High levels of flavonoids are produced throughout the endosperm of GT rice, while size of kernel is significantly reduced. To date, it is the first report that endosperm of cereals produce flavonoids, even though there have been cases of cereal varieties that.

Although no difference in growing behavior between the GT rice and the wild type was found, maturation of kernels was greatly delayed in the GT rice. This can be explained by a role of flavonoids, in general, in auxin transport. It might be possible that inhibition of auxin transport within the endosperm results in delayed or reduced production of ethylene that is directly responsible for kernel maturation such as induction of dehydration and senescence.

Choice of promoters for transgenes seems to be critical in production transgenic crops with expected phenotype. Expression of the transgenes was specifically directed in the endosperm. Prolamin NPR33 promoter is endosperm-specific but slightly leaky in vegetative tissues such as per.

Reduced kernel size resulted from inhibition of grain filling or problem with carbohydrate metabolism. There is intrusion of pericarp into the inner endosperm, found in kernel sections. Starchy endosperm rather than vitreous indicates that endosperm development is abnormal. Not all genes are activated by the transgenes.

LC/MS/MS results of the major peaks and color reaction data suggest that the flavonoid biosynthetic pathway was activated up to the step of dihydroflavonols, from which various derivatives were generated by various modifications. Similar results were reported by the group (2002) who generated C1/LC transgenic tomato lines. Their case was different from ours for such and such.

Tissue-specificity of flavonoid biosynthesis: ectopic expression of chalcone isomerase results in a huge increase in flavonols in the peel tissue, but not in the flesh tissue (Verhoeyen, 2002).

Estimated total flavonoid content in the GT rice seems to be reasonable, because the sum of major peaks is slightly less than the estimated total content. In addition, the total content of flavonoids in the green tea leaves falls into the ranges that are reported in other studies, which is from 10 to 20% of dry weight.

Delayed kernel maturation of the transgenic rice may be associated with altered metabolism or transport of plant hormones such as auxin, cytokinin, ABA, GA and ethylene. Buer and Muday (2004) reported that flavonoids negatively affect basipetal transport of auxin in *Arabidopsis* roots, which, in turn, accelerates root bending in response to gravity.

REFERENCES

Bovy, A., de Vos, R., Kemper, M., Schijlen, E., Almenar Pertejo, M., Muir, S., Collins, G., Robinson, S., Verhoeyen, M., Hughes, S., Santos-Buelga, C. and van Tunen, A. (2002) High-flavonol tomatoes resulting from the heterologous expression of the maize transcription factor genes LC and C1. *Plant Cell* 14, 2509-2526.

Cahoon, E. B., Hall, S. E., Ripp, K. G, Ganzke, T. S., William D Hitz, W. D. and Coughlan, S. J. (2003) Metabolic redesign of vitamin E biosynthesis in plants for tocotrienol production and increased antioxidant content. *Nature Biotechnology* 21, 1082-1087

Dixon, R. A. and Steele, C. L. (1999). Flavonoids and isoflavonoids—a gold mine for metabolic engineering. *Trends in plant science* 4, 394-400.

Enomoto. S., Okada, Y, Guvenc, A., Erdurak, C. S., Coskun, M. and Okuyama, T. (2004) Inhibitory effect of traditional Turkish folk medicines on aldose reductase (AR) and hematological activity, and on AR inhibitory activity of quercetin-3-O-methyl ether isolated from *Cistus laurifolius L. Biol. Pharm. Bull.* 27, 1140-1143.

Buer, C S and Muday, G K (2004) The transparent testa4 mutation prevents flavonoid synthesis and alters auxin transport and the response of *Arabidopsis* roots to gravity and light. *Plant Cell* 16: 1191-1205.

Wattel A, Kamel S, Prouillet C, Petit J P, Lorget F, Offord E, Brazier M. (2004) Flavonoid quercetin decreases osteoclastic differentiation induced by RANKL via a mechanism involving NF kappa B and AP-1. J Cell Biochem 92(2):285-95.

Aherne S A, O'Brien N M. (2000). Mechanism of protection by the flavonoids, quercetin and rutin, against tert-butyl-hydroperoxide- and menadione-induced DNA single strand breaks in Caco-2 cells. Free Radic Biol Med 29(6): 507-14.

Xu J Z, Yeung S Y, Chang Q, Huang Y, Chen Z Y. (2004). Comparison of antioxidant activity and bioavailability of tea epicatechins with their epimers. Br J Nutr 91(6): 873-81.

Singh J P, Selvendiran K, Banu S M, Padmavathi R, Sakthisekaran D. (2004). Protective role of Apigenin on the status of lipid peroxidation and antioxidant defense against hepatocarcinogenesis in Wistar albino rats. Phytomedicine 11(4): 309-14.

Ling W H, Wang L L, Ma J. (2002). Supplementation of the black rice outer layer fraction to rabbits decreases atherosclerotic plaque formation and increases antioxidant status. J Nutr. 132(1): 20-6.

Holton, T. A. and Cornish, E. C. (1995) Genetics and biochemistry of anthocyanin biosynthesis. *Plant Cell* 7, 1071-1083.

Howitz, K. T., Bitterman, K. J., Cohen, H. Y., Lamming, D. W., Lavu, S., Wood, J. G., Zipkin, R. E., Chung, P., Kisielewski, A., Zhang, L-L., Scherer, B. and Sinclair, D. A. (2003) Small molecule activators of sirtuins extend *Saccharomyces cerevisiae* lifespan. *Nature* 425, 191-196

Hu, J., Reddy, V. S. and Wessler, S. R. (2000) The rice R gene family: two distinct subfamilies containing several miniature inverted-repeat transposable elements. *Plant Mol. Biol.* 42, 667-78.

Jankun, J., Selman, S. H., Swiercz, R. and Skrzypczak-Jankun, E. (1997) Why drinking green tea could prevent cancer. *Nature* 387, 561.

Lloyd, A. M., Schena, M., Walbot, V. and Davis, R. W. (1994) Epidermal cell fate determination in *Arabidopsis*: patterns defined by a steroid-inducible regulator. *Science* 266, 436-439.

Pinent, M., Blay, M., Blade, M. C., Salvado, M. J., Arola, L. and Ardevol, A. (2004) Grape seed-derived procyanidins have an antihyperglycemic effect in streptozotocin-induced diabetic rats and insulinomimetic activity in insulin-sensitive cell lines. *Endocrinology* 145, 4985-4990.

Quattrocchio, F., Wing, J. F., Leppen, H., Mol, J. and Koes, R. E. (1993) Regulatory genes controlling anthocyanin pigmentation are functionally conserved among plant species and have distinct sets of target genes. *Plant Cell* 5, 1497-1512.

Quattrocchio, F., Wing, J. F., van der Woude, K., Mol, J. N. and Koes, R. (1998) Analysis of bHLH and MYB domain proteins: species-specific regulatory differences are caused by divergent evolution of target anthocyanin genes. *Plant J.* 13, 475-488.

Ren, W., Qiao, Z., Wang, H. and Zhang, L. (2003) Flavonoids: Promising Anticancer Agents. *Medicinal Research Reviews* 23: 519-534.

Sambrook, J. and Russell, D. W. (2001) Molecular Cloning: A Laboratory Manual. Vol 1, Cold Spring Harbor Laboratory Press, Cold Spring Harbor, N.Y., pp 7.4-7.8.

Schijlen, E. G, Ric de Vos, C. H., van Tunen, A. J. and Bovy, A. G (2004) Modification of flavonoid biosynthesis in crop plants. *Phytochemistry* 65, 2631-2648.

Shirley B. W. (1996) Flavonoid biosynthesis: 'new' functions for an 'old' pathway. *Trends in Plant Science* 1, 377-382.

Sharp, R. N. (1991) Rice: Production, processing, and utilization. In: Lorenz, K. J. and Kulp, K. (eds), Handbook of cereal science and technology. Marcel Dekker, Inc., New York, pp 301-329.

Verhoeyen, M. E., Bovy, A., Collins, G., Muir, S., Robinson, S., de Vos, C. H. and Colliver, S. (2002) Increasing antioxidant levels in tomatoes through modification of the flavonoid biosynthetic pathway. *J. Exp. Bot.* 53, 2099-2106.

Williams, R. J., Spencer, J. P. and Rice-Evans, C. (2004) Flavonoids: antioxidants or signaling molecules? *Free Radic. Biol. Med.* 36, 38-49.

Winkel-Shirley B. (2001a) Flavonoid biosynthesis. A colorful model for genetics, biochemistry, cell biology, and biotechnology. *Plant Physiol.* 126, 485-493.

Winkel-Shirley B. (2001b) It takes a garden. How work on diverse plant species has contributed to an understanding of flavonoid metabolism. *Plant Physiol.* 127, 1399-1404.

Winkel-Shirley B. (2002) Biosynthesis of flavonoids and effects of stress. *Current Opinion in Plant Biology* 5, 218-223.

Ye, X., Al-Babili, S., Kloti, A., Zhang, J., Lucca, P., Beyer, P. and Potrykus, I. (2000) Engineering the provitamin A (beta-carotene) biosynthetic pathway into (carotenoid-free) rice endosperm. *Science* 287, 303-305.

Yousef, M. I., Kamel, K. I., Esmail, A. M. and Baghdadi, H. H. (2004) Antioxidant activities and lipid lowering effects of isoflavone in male rabbits. *Food Chem. Toxicol.* 42, 1497-1503.

---

What is claimed is:

1. A transgenic rice having high levels of various flavonoids selected from the group consisting of dihydroquercetin (taxifolin), dihydroisorhamnetin (3'-O-methyl taxifolin), and 3'-O-methyl quercetin in kernel which is grown from a transgenic rice cell, wherein the transgenic rice cell is transformed by an expression vector comprising:

(a) a polynucleotide of maize C1 gene given in SEQ ID NO: 1;

(b) a polynucleotide of maize R-S gene given in SEQ ID NO: 2; and (c) regulatory sequences comprising a rice 13-kD prolamin gene promoter given in SEQ ID NO: 3 operatively linked to the polynucleotide.

2. The transgenic rice of claim 1, wherein the levels of dihydroquercetin (taxifolin), dihydroisorhamnetin (3'-O-methyl taxifolin), and 3'-O-methyl quercetin are 120~180 μg per gram, 270~390 μg per gram, and 40~70 μg per gram of dried kernels respectively.

3. The transgenic rice of claim 1, wherein total flavonoids is more than 12 mg per gram of dried kernels.

* * * * *